United States Patent [19]

Daggy et al.

[11] Patent Number: 5,356,618
[45] Date of Patent: Oct. 18, 1994

[54] PSYLLIUM DRINK MIX COMPOSITIONS

[75] Inventors: Bruce P. Daggy; Lee A. Hord, both of Mason, Ohio

[73] Assignee: The Procter & Gamble Company, Cincinnati, Ohio

[21] Appl. No.: 62,369

[22] Filed: May 14, 1993

[51] Int. Cl.⁵ ............................................. A61K 35/78
[52] U.S. Cl. .................. 424/78.01; 424/78.1
[58] Field of Search ...................... 424/78.1; 424/78.01

[56] References Cited

U.S. PATENT DOCUMENTS

| | | | |
|---|---|---|---|
| 4,883,788 | 11/1989 | Day et al. | 514/57 |
| 4,950,140 | 8/1990 | Pflaumer et al. | 424/439 |
| 4,978,529 | 12/1990 | Denick, Jr. | 424/195.1 |
| 4,996,051 | 2/1991 | Meer et al. | 424/195.1 |
| 4,999,200 | 3/1991 | Casillan | 424/480 |
| 5,009,916 | 4/1991 | Colliopoulos | 426/615 |
| 5,023,245 | 6/1991 | Kuhrts | 424/439 |
| 5,048,760 | 9/1991 | Barbera et al. | 241/9 |
| 5,126,150 | 6/1992 | Piatt et al. | 426/94 |
| 5,149,541 | 9/1992 | Leis et al. | 424/489 |
| 5,219,570 | 6/1993 | Barbera | 424/195.1 |
| 5,223,298 | 6/1993 | Wullschleger et al. | 424/439 |
| 5,232,698 | 8/1993 | Hord et al. | 424/195.1 |
| 5,234,687 | 8/1993 | Barbera et al. | 424/195.1 |
| 5,234,916 | 8/1993 | Hord | 424/95.1 |

OTHER PUBLICATIONS

Goodman and Gilman, The Pharmacologic Basis of Therapeutics, 6th Edition, 1004 and 1007 (1980).
Garvin et al., Proc. Soc. Exp. Biol. Med., 120, 744–746 (1965).
Forman et al., Proc. Soc. Exp. Biol. Med., 127, 1060–1063 (1968).
Anderson et al., Fed. Proc., 46, 877 (1987).
Anderson et al., Am. J. Gastroenterology, 81, 907–919 (1986).
Fagerberg, Curr. Ther. Res., 31, 166 (1982).

*Primary Examiner*—Thurman K. Page
*Assistant Examiner*—Peter F. Kulkosky
*Attorney, Agent, or Firm*—Mary Catherine Poland; Kathleen M. Harleston; Kim William Zerby

[57] ABSTRACT

Psyllium husk-containing drink mix compositions comprising calcium citrate malate.

20 Claims, No Drawings

PSYLLIUM DRINK MIX COMPOSITIONS

BACKGROUND OF THE INVENTION

The present invention relates to psyllium husk-containing drink mix compositions comprising the salt calcium citrate realate. This salt provides the benefit of reducing the gellation rate of the psyllium husk when dispersed in an aqueous solution.

Products containing psyllium seed husk are known (for example, Metamucil®, sold by The Procter & Gamble Company). Such products are useful for the benefit of normalizing bowel function and laxation. In addition, recent research has demonstrated the effectiveness of psyllium seed husk fiber in reducing human serum cholesterol levels and in controlling blood glucose levels in diabetics.

Psyllium seed husk contains natural mucillage. It forms a gellatinous mass on contact with water, and it exhibits poor dispersibility and mixability in water. Dispersibility and mixability of psyllium husk in aqueous solutions have been shown to be improved by utilizing higher levels of sugar, and by coating the husk with materials such as maltodextrin.

Once dispersed in the aqueous solution, the psyllium husk begins to gel with an accompanying increase in the viscosity of the drink solution. Typically, the consumer of the psyllium husk suspension drinks the liquid suspension in a relatively short period of time (less than about two minutes) in order to avoid having to drink an aesthetically unacceptable high viscosity liquid (i.e., the solution is considered too thick to enjoy drinking or difficult to drink). By reducing the psyllium husk particle size it is possible to eliminate the gritty texture of the psyllium husk yet maintain efficacy. However, the smaller the particle size of the psyllium husk, the more the rapid gellation rate is a consumer noticeable concern.

For these reasons, there continues to be a need for psyllium husk drink mix compositions having reduced (slower) gellation rates and improved aesthetics. One way to control the rate of gellation is by using acids to reduce the pH of the drink mix solution. Salts of certain organic acids at certain levels can have the unwanted effect of increasing the gellation rate (i.e., make the solution thicker, faster), but when used at other levels may provide the desired benefit of reducing the gellation rate. However, it has been discovered that calcium citrate malate provides a beneficial gellation rate reduction, which is particularly surprising in view of the fact that the potassium salt of citric acid can increase the gellation rate of psyllium at certain levels.

The present invention is therefore directed to adding calcium citrate malate to psyllium husk-containing drink mix compositions to improve the aesthetics of the drink compositions. For example, for the larger particle size psyllium husk which is less readily suspended, the husk which settles to the bottom of the glass may have improved aesthetics such as lower viscosity for the last portions of the drink. For the smaller particle size husk which is more readily suspended, the aesthetics may be improved by the liquid suspension having a reduced gellation rate.

It is therefore an object of the present invention to provide improved psyllium husk drink mix compositions having reduced gellation rates in aqueous solution and/or improved aesthetics. A further object is to provide psyllium drink mix compositions which contain an aesthetically-acceptable source of dietary calcium.

These and other objects of the present invention will become readily apparent from the detailed description which follows.

All percentages and ratios used herein are by weight unless otherwise specified. Screen mesh sizes used herein are based on U.S. standards.

SUMMARY OF THE INVENTION

The present invention relates to psyllium husk-containing drink mix compositions. Such compositions comprise: (a) from about 10% to about 99% psyllium husk; (b) from about 0.1% to about 75% of calcium citrate malate; and (c) from about 0% to about 90% carrier materials; and wherein further said composition is in a form mixable with a liquid to form a suspension of the psyllium husk.

DETAILED DESCRIPTION OF THE INVENTION

The drink mix compositions of the present invention are psyllium-containing compositions in any form suitable for mixing with a liquid to form a psyllium husk suspension for oral consumption. A preferred form is a dry powder in bulk or unit dose form which readily mixes and disperses in the liquid. The components of the compositions according to the present invention, and representative amounts, are described in detail as follows.

Psyllium Husk

The psyllium husk used in the present invention is from psyllium seeds, from plants of the *Plantago* genus. Various species such as *Plantago lanceolate, P. rugelii*, and *P. major* are known. Commercial psyllium husk include the French (black; *Plantago indica*), Spanish (*P. psyllium*) and Indian (blonde; *P. ovata*). Indian (blonde) psyllium husk is preferred for use herein. Also preferred is psyllium husk which is at least about 85% pure, more preferably at least about 90% pure, and most preferably at least about 95% pure.

The psyllium husk is obtained from the seed coat of the psyllium seeds. It is typical to remove the seed coat from the rest of the seed by, for example, slight mechanical pressure, and then to use only the seed coat. The seed coat is preferably removed and sanitized by methods known in the art. Preferred is sanitized psyllium seed husk having substantially intact cell structure, the sanitization having been accomplished by methods such as ethylene oxide sanitization and superheated steam sanitization (as taught in U.S. Pat. No. 4,911,889, issued Mar. 27, 1990 to Leland et. al., the disclosures of which are incorporated herein by reference in their entirety). It is also preferred that the psyllium husk herein has reduced particle size (as taught, for example, in U.S. Pat. No. 5,149,541, issued Sep. 22, 1992, to Leis, Jr. et al., the disclosures of which are incorporate herein by reference in their entirety).

Preferred psyllium husk utilized in compositions of the present invention have a substantial amount of small particle size psyllium husk such that the psyllium husk comprises psyllium husk particle sizes distributed such that more than about 90% is smaller than about 45 mesh. More preferably, more than about 80% is smaller than about 50 mesh, further preferred is more than about 80% is smaller than about 60 mesh, and most preferably at least about 80% is smaller than about 80 mesh. Further preferred particle sizes are distributed as follows: less than about 25% larger than about 60 mesh, and at least about 40% smaller than about 80 mesh. More preferred are particle size distribution of: less than about 10% larger than about 60 mesh, at least about 40% within the range of from about 80 mesh to about 200 mesh, and less than about 50% smaller than about 200 mesh. Particle sizes and particle size distributions may be readily determined by one of ordinary skill in the art, for example by sieving using an Alpine Laboratory Air Jet Sieve, Type 200 LS (sold by Alpine American Corp., Natick Mass.).

The drink mix compositions preferably contain from about 10% to about 99%, more preferably from about 20% to about 90%, most preferably from about 25% to about 75%, of psyllium husk.

Calcium Citrate Malate

As used herein, the term "calcium citrate malate" refers to a mixture or (preferably) a complex of calcium, citrate and malate. The calcium citrate malate may consist of a mixture of calcium citrate and calcium malate, a complex of calcium containing citrate and malate ligands, a mixture of a calcium salt with citric acid and malic acid, or combinations thereof. Calcium citrate malate is a highly bioavailable source of calcium. Calcium citrate malate for use herein may be preformed as a powder or can be formed in situ.

The calcium citrate malate to be present in the compositions according to this invention preferably comprises the components in the following molar ratios. The molar ratio of citrate in the salt is from about 1 to about 3 and the molar ratio of malate is from about 1 to about 5. The molar ratio of calcium is from about 2 to about 8. The ratio of total moles calcium:total moles citrate:total moles malate is preferably from about 2:1:1 to about 8:2:1, more preferably from about 4:2:3 to about 6:3:4. The calcium citrate malate may contain other acid anions in addition to citrate and malate. Such anions may include, for example, carbonate, hydroxide, phosphate and mixtures thereof depending on the calcium source.

Preferably, the calcium citrate malate is neutral, comprised entirely of citrate and malate anions. Thus, preferably, the equivalents of calcium (2×moles calcium) is about equal to the total number of equivalents of citrate (3×moles citrate) plus malate (2×moles malate). Preferred calcium citrate malate have calcium: citrate:malate molar ratios of about 6:2:3 and 4:2:3.

Calcium citrate malate for use in solid forms may be made, for example, by first dissolving citric acid and malic acid in the desired molar ratio in water. Calcium carbonate may then be added to the solution in such an amount that the ratio of moles of calcium to moles citrate and moles malate is as desired. Carbon dioxide will be evolved. The solution may then be dried (as by freeze drying of oven drying at temperatures below 100° C.) to obtain the calcium citrate malate. Methods for making calcium citrate malate are described in the following documents, incorporated by reference herein in their entirety: Japanese Patent Specification SHO 56-97248, Kawai, published Aug. 5, 1981; U.S. Pat. No. 4,722,847, issued to Heckert, Feb. 2, 1988; and U.S. Pat. No. 5,186,965, issued to Fox et al., Feb. 16, 1993.

Most preferred drink mix compositions according to the present invention comprise as all or part of the calcium citrate malate a complex of calcium citrate malate in a molar ratio of from about 6:2:3 to about 4:2:3. This complex may be prepared prior to preparing the present invention psyllium compositions by methods such as those taught, for example, by U.S. Pat. No. 5,186,965, to Fox et al., issued Feb. 16, 1993, incorporated herein by reference in its entirety. This complex may be dry blended with the psyllium composition, or included within psyllium-containing granules or agglomerates by coating a blend of the complex and psyllium with a coating or binder material, or by coating the psyllium with a solution containing some or all of the complex and then drying.

The level of the calcium citrate malate is sufficient to reduce the gellation rate of the psyllium husk relative to the compositions without added salt. Determination of whether the level of calcium citrate malate present in the psyllium husk-containing composition is a level whereby the gellation rate of the psyllium husk in an aqueous solution is reduced is readily made by simple experimentation, e.g. by comparing the rate of viscosity increase for the psyllium husk in a composition containing the calcium citrate malate versus the composition containing the same components but not the calcium citrate malate or other added salts. Methods and equipment for measuring gellation rates and viscosity of psyllium husk are known, and such measurements and determinations can easily be made by one skilled in the art. For example, the Brookfield Viscometer may be used.

Compositions of the present invention therefore may comprise from about 0.1% to about 75% calcium citrate malate, preferably from about 0.1% to about 20%, and more preferably from about 0.5% to about 10% by weight of the drink mix composition.

Optional Carrier Materials

Optional carrier materials useful for the compositions of the present invention must be safe for oral administration to humans, and may be chosen by one of ordinary skill in the art as appropriate for the drink mix form and use intended for the product. Psyllium-containing drink mix products, methods for making, and carrier materials useful for these products, are described more fully, for example, in U.S. Pat. No. 4,459,280, to Colliopoulos et al., issued Jul. 10, 1984; U.S. Pat. No. 4,548,806, to Colliopoulos et al., issued Oct. 22, 1985; U.S. Pat. No. 4,321,263, to Powell et al., issued Mar. 23, 1982; and U.S. Pat. No. 4,828,842, to Furst et al., issued May 9, 1989; all of which are incorporated by reference herein in their entirety. The drink mix compositions of the present invention comprise from about 0% to about 90%, preferably from about 10% to about 80%, and more preferably from about 25% to about 75%, of carrier materials.

Most preferred are products of the present invention in dry powder form suitable for mixing in a liquid to form a psyllium-containing drink. Preferred carrier materials for such powder forms are known and are also described in detail, for example, in U.S. Pat. Nos. 4,459,280 and 4,548,806, incorporated hereinbefore by reference. Preferred are such powders (preferably sugar free) comprising maltodextrin. Also especially preferred are powders comprising agglomerates of psyllium and/or coated psyllium, especially agglomerated with maltodextrin and/or sucrose.

Agglomerating materials preferred for use herein are therefore known. These agglomerating materials include those selected from the group consisting of water dispersible hydrolyzed starch oligosaccharide, monosaccharide, di-saccharide, polyglucose, polymaltose, and mixtures thereof. Compositions of the present invention preferably comprise from about 0.5% to about 20% of agglomerating material coating on said psyllium husk, preferably from about 1% to about 10%, and more preferably from about 1% to about 5%.

Hydrolysis of starch may be accomplished by a reaction of either acid, enzymes (e.g., alpha-amylase, beta-amylase or amyloglucosidase), or a combination of the two either together or reacted in series. The hydrolysis will follow different pathway depending on whether acids or enzymes are used. The result is a mixture of oligosaccharides which may be separated for their different properties. The resulting separated water dispersible (preferably soluble) hydrolyzed starch oligosaccharides are classified by their reducing sugar content, i.e., the mono- or di-saccharides such as glucose or fructose. The percent reducing sugar content in the particular hydrolyzed starch oligosaccharide is measured on a weight/weight basis as the Dextrose Equivalent (or "D.E."). Hydrolyzed starch oligosaccharides with a D.E. of from 0 to 20 are called maltodextrins. The solid maltodextrins have low to moderate sweetness, low to moderate hygroscopicity, solubility in water and alcohol, and have reduced browning. Above a D.E. of about 20 the hydrolyzed starch oligosaccharides are called syrup solids. The syrup solids are soluble but have a more noticeable sweetness and are more hydroscopic. Above a D.E. of about 30, the syrup solids become less desirable for use herein. A preferred water dispersible hydrolyzed starch oligosaccharide therefore has a D.E. of from about 0 to about 30. A preferred maltodextrin has a D.E. of from about 5 to about 20, more preferably about 10 (i.e., a reducing sugar content ratio of 10% w/w of the oligosaccharide).

The mono-saccharides are those carbohydrates that in general are aldehyde-alcohols or ketone alcohols that are a hexose or pentose and have a sweet taste. They are readily soluble in water and form crystalline solids. Examples of the di-saccharides are those carbohydrates which yield two mono-saccharides on hydrolysis. Examples of di-saccharides are lactose, sucrose and maltose.

Compositions of the present invention may also comprise as part or all of the optional carrier material an edible acid in addition to citric acid or malic acid. The term "edible acids", as used herein, means any water soluble acid material having a pKa of less than about 5, preferably within the range of from about 2 to about 5, and is safe for ingestion by humans. Examples of such edible acids include, but are not limited to, ascorbic acid, succinic acid, tartaric acid, phosphoric acid, monopotassium phosphate, and mixtures thereof. The compositions of the present invention may comprise from about 0.1% to about 25% edible acid in addition to citric acid and/or malic acid, preferably from about 0.1% to about 10%, and more preferably from about 0.1% to about 5%.

Preferred compositions of the present invention are those which have some or all of the psyllium husk agglomerated. Preferred is single layer coating of the psyllium husk to agglomerate the husk. This may be achieved by utilizing equipment (referred to herein as single pass fluidizing powder wetting apparatus) which operates preferably by dropping a dry blend psyllium-containing material through a highly turbulent annular zone formed by a cylindrical wall and a rotating shaft with variously pitched attached blades. A solution mixture or water is preferably sprayed into this zone to contact a dry psyllium-containing blend. The resulting coated, preferably agglomerated, psyllium husk is dropped to a fluid bed dryer where the added solvent is removed. An example of this equipment is the Bepex Turboflex Model No. TFX-4 (sold by Bepex Corporation; Minneapolis, Minn.) with a six square foot bed vibrating fluid bed dryer (sold by Witte Corporation, Inc.; Washington, N.J.).

The psyllium-containing blend preferably comprises from about 25% to about 100% of psyllium. Optional components for the psyllium-containing blend include, but are not limited to, some or all of the calcium citrate malate, edible acid (including citric acid and/or malic acid), sweetening agents (preferably low calorie sweetening agents including, but not limited to, aspartame, saccharin, cyclamate, acesulfame, and mixtures thereof), flavoring agents, coloring agents, agglomerating materials (especially maltodextrin), dietary fibers such as brans (e.g., wheat bran; oat bran; rice bran) and/or pharmaceutical agents (e.g., aspirin; non-steroidal antiinflammatories; sennosides; cholesterol lowering agents, e.g., anion exchange resins such as cholestyramine and cholestipol); and some or all of these optional components may be included in the solution mixture sprayed on the psyllium blend or added by simple blending with the psyllium composition later in the manufactureing process. As noted hereinbefore, it is preferred that the psyllium-containing blend be dry, but it is possible to utilize suitable solvents (e.g., alcohols and/or water) if one is careful, especially if water is utilized, not to cause substantial hydration and swelling of the psyllium, since this is expected to adversely affect the rate at which psyllium husk can interact with water or other fluids.

The solution mixture preferably comprises one or more edible acids (including citric acid and/or malic acid) to be sprayed onto the psyllium-containing blend along with also preferably comprising some or all of the calcium citrate malate. This may be prepared by selecting a liquid (e.g., alcohol and/or water) as appropriate for the materials being coated onto the psyllium husk. However, it is preferred that water be utilized. Preferred is also spraying the solution mixture onto a dry psyllium-containing blend. Preferably, when a spraying technique is used, the solution mixture is a saturated or concentrated aqueous solution of the calcium citrate malate; also preferred is the solution mixture comprising edible acid in addition to citric acid and/or malic acid. It is also optionally possible to repeat the coating and drying steps, thereby building up a coating on the psyllium husk which comprises several thin layers of the materials. In addition, other optional materials may be present in the solution mixture, such as coloring agents, pharmaceutical agents, and mixtures thereof.

Other methods for preparing compositions according to the present invention include dry blending the ingredients and other means of multiple layer coating of the psyllium husk. The latter may be accomplished by using, for example, fluid bed agglomerating equipment such as the Fluid Air, Inc. Model 0300 Granulator-Dryero.

Method of Treatment

The present invention also relates to a method for providing laxation and regulating bowel function for a human in need of such treatment. This method comprises administering to a human in need of such treatment a safe and effective amount of a psyllium-containing composition of the present invention. Ingestion of from about 2.5 grams to about 30 grams per day of the psyllium fiber in a composition according to the present invention is appropriate in most circumstances to produce laxation. However, this can vary with the size and condition of the patient, and such matters will, of course, be apparent to the attending physician. However, since the psyllium material is nontoxic, even higher ingestion levels can be used without undue side effects. A typical dose for laxation purposes involves administering from about 3 to about 15 grams of psyllium fiber in one dose.

The present invention further relates to methods for reducing serum cholesterol levels in humans. These methods comprise orally administering to a human in need of having a lowered blood cholesterol level a safe and effective amount of an aqueous liquid suspension of a psyllium-containing composition of the present invention. Ingestion of compositions of the present invention comprising amounts sufficient to administer from about 2.5 grams to about 30 grams per day of psyllium fiber, preferably from about 5 grams to about 15 grams, is appropriate in most circumstances. However, this can vary with the size and condition of the patient, and the patient's blood cholesterol level. Such matters will, of course, be apparent to the attending physician. However, since the psyllium material is nontoxic, even higher ingestion levels can be used without undue side effects, keeping in mind the materials herein have the hereinbefore noted laxative effect.

Treatment of the patient to reduce serum cholesterol levels comprises chronic ingestion in order to lower and maintain the lowered cholesterol levels. Daily ingestion is preferred, and a daily ingestion of from about 5 grams to about 15 grams of the psyllium fiber is most commonly used, with said ingestion preferably being 1 to 3 times per day. Again, depending on the patient's size and cholesterol level in the patient's blood, this can be varied.

The following examples further describe and demonstrate embodiments within the scope of the present invention. These examples are given solely for the purpose of illustration and are not to be construed as limitations of the present inventions as many variations thereof are possible without departing from the spirit and scope.

EXAMPLE 1

| Components | Weight % |
| --- | --- |
| Psyllium[1] | 55.0 |
| Maltrin[2] | 39.4 |
| CCM[3] | 5.3 |
| Citric Acid | 0.3 |

[1] Psyllium husk of particle size 100% through 80 mesh.
[2] Maltodextrin
[3] Calcium citrate malate complex having the molar ratio 6:2:3.

This psyllium drink mix composition according to the present invention is prepared by agglomerating by spraying a dry blend of the psyllium husk and maltrin with an aqueous solution of citric acid in a single pass agglomerator (as described in detail in European Patent Publication No. 412,604, published Feb. 13, 1991, the disclosures of which are incorporated herein by reference in their entirety) and subsequently dried in a fluidized bed dryer. The calcium citrate malate is then dry blended into the composition. Consumption of one teaspoon of this composition as a suspension in 8 ounces of water is effective for providing laxation for a patient in need of such benefit.

EXAMPLE 2

| Components | Weight % |
| --- | --- |
| Regular Flavor Metamucil ®[1] | 97% |
| CCM[2] | 3% |

[1] Contains large particle size psyllium husk and dextrose.
[2] Calcium citrate malate complex having the molar ratio 4:2:3.

This psyllium drink mix composition according to the present invention is prepared by dry mixing the ingredients. One teaspoon of this composition mixed with 8 ounces of water provides a drink having improved aesthetics and is effective for providing laxation for a patient in need of such benefit.

EXAMPLE 3

To evaluate the value of adding various levels of calcium citrate malate, the following comparative testing was conducted to evaluate the rate of viscosity increase for small particle size psyllium husk suspended in water. The suspensions were prepared using the following components:

| Suspension #: | Weight %[e] | | | | |
| --- | --- | --- | --- | --- | --- |
| | 1 | 2 | 3 | 4 | 5 |
| psyllium[a] | 56.6 | 56.7 | 53.6 | 55.1 | 55.9 |
| maltrin[b] | 40.8 | 42.9 | 40.6 | 41.7 | 42.3 |
| citric acid | 0.35 | 0.35 | 0.33 | 0.34 | 0.34 |
| CCM[c] | — | — | 5.46 | 2.81 | 1.42 |
| Magnesium sulfate | 2.2[d] | — | — | — | — |

[a] approximately 100% smaller than about 80 mesh.
[b] maltodextrin
[c] Calcium citrate malate complex having the molar ratio 6:2:3.
[d] Anhydrous weight.
[e] Weight percent is prior to water addition; water was used for the suspensions to provide 480 g of solution, either 480 g of water or 480 g of a water/calcium citrate malate solution.

Dry blends of psyllium and maltrin were agglomerated by using a Glatt Fluid Bed Drier for a process whereby either a citric acid solution or a citric acid/magnesium sulfate solution was used to agglomerate the blend. These preparations, in amounts sufficient to give approximately 9.5 g psyllium (Suspension #1:9.4 g; Suspensions #'s 2–5:9.6 g), were then mixed with water or a calcium citrate malate solution (0.2% diluted as necessary to provide the CCM present in the Suspensions #'s 3–5) in a 600 ml beaker, and the viscosity of the suspensions were measured using a Brookfield Viscometer (Model RVT; Spindle #1; 10 rpm).

| Suspension #: | 1 | 2 | 3 | 4 | 5 |
| --- | --- | --- | --- | --- | --- |
| Time (seconds) | Viscosity (centipoise) | | | | |
| 60 | 65 | n.d. | 80 | n.d. | 125 |
| 90 | 190 | 710 | 200 | 235 | 305 |
| 120 | 330 | >1000 | 335 | 395 | 500 | n.d. = not determined.

The results of these measurements demonstrate that the addition of calcium citrate malate to a psyllium-containing drink mix provides the benefit of reducing the gellation rate of the psyllium (compare Examples 3, 4, and 5 with Example 2). The addition of calcium citrate malate can also provide a gellation control benefit comparable to the addition of magnesium sulfate (Example 1 compared with Example 3).

What is claimed is:

1. A psyllium husk-containing drink mix composition comprising:
   (a) from about 10% to about 99% psyllium husk;
   (b) from about 0.1% to about 75% of calcium citrate malate; and
   (c) from about 0% to about 90% carrier material; and wherein further said composition is in a form mixable with a liquid to form a suspension of the psyllium husk.

2. The composition according to claim 1 wherein the calcium citrate malate comprises the components such that the molar ratio of citrate is from about 1 to about 3 and the molar ratio of malate is from about 1 to about 5 and the molar ratio of calcium is from about 2 to about 8.

3. The composition according to claim 1 wherein the calcium citrate malate comprises the components in the ratio of total moles calcium:total moles citrate:total moles malate of from about 2:1:1 to about 8:2:1.

4. A psyllium husk-containing drink mix composition comprising:
   (a) from about 20% to about 90% psyllium husk;
   (b) from about 0.1% to about 20% calcium citrate malate;
   (c) from about 10% to about 80% carrier material; and wherein further said composition is in a form mixable with a liquid to form a suspension of the psyllium husk.

5. The composition according to claim 4 wherein the calcium citrate malate comprises the components in the ratio of total moles calcium:total moles citrate:total moles malate of from about 4:2:3 to about 6:3:4.

6. The composition according to claim 4 wherein the calcium citrate malate is selected from the group consisting of about 6:2:3 calcium:citrate:malate and about 4:2:3 calcium:citrate:malate.

7. The composition according to claim 4 comprising maltodextrin.

8. The composition according to claim 4 wherein the psyllium husk is coated.

9. The composition according to claim 6 wherein the psyllium husk is coated with maltodextrin.

10. A method for providing laxation for humans, said method comprising orally administering to a human in need of laxation a safe and effective amount of a liquid suspension of the psyllium husk-containing composition according to claim 1.

11. A method for providing laxation for humans, said method comprising orally administering to a human in need of laxation a safe and effective amount of a liquid suspension of the psyllium husk-containing composition according to claim 3.

12. A method for providing laxation for humans, said method comprising orally administering to a human in need of laxation a safe and effective amount of a liquid suspension of the psyllium husk-containing composition according to claim 6.

13. A method for providing laxation for humans, said method comprising orally administering to a human in need of laxation a safe and effective amount of a liquid suspension of the psyllium husk-containing composition according to claim 8.

14. A method for providing laxation for humans, said method comprising orally administering to a human in need of laxation a safe and effective amount of a liquid suspension of the psyllium husk-containing composition according to claim 9.

15. A method for reducing serum cholesterol levels in humans, said method comprising orally administering to a human in need of such treatment a safe and effective amount of a liquid suspension of the psyllium husk-containing composition according to claim 1.

16. A method for reducing serum cholesterol levels in humans, said method comprising orally administering to a human in need of such treatment a safe and effective amount of a liquid suspension of the psyllium husk-containing composition according to claim 3.

17. A method for reducing serum cholesterol levels in humans, said method comprising orally administering to a human in need of such treatment a safe and effective amount of a liquid suspension of the psyllium husk-containing composition according to claim 6.

18. A method for reducing serum cholesterol levels in humans, said method comprising orally administering to a human in need of such treatment a safe and effective amount of a liquid suspension of the psyllium husk-containing composition according to claim 8.

19. A method for reducing serum cholesterol levels in humans, said method comprising orally administering to a human in need of such treatment a safe and effective amount of a liquid suspension of the psyllium husk-containing composition according to claim 1 further comprising a cholesterol lowering agent.

20. A method for reducing serum cholesterol levels in humans, said method comprising orally administering to a human in need of such treatment a safe and effective amount of a liquid suspension of the psyllium husk-containing composition according to claim 3 further comprising an anion exchange resin.

* * * * *